(12) United States Patent
Shirotani et al.

(10) Patent No.: US 11,642,247 B2
(45) Date of Patent: May 9, 2023

(54) PRESSURE-SENSITIVE ADHESIVE SHEET, ADHESIVE BANDAGE, AND METHOD OF PRODUCING THE SAME

(71) Applicant: KURARAY CO., LTD., Kurashiki (JP)

(72) Inventors: Yasuhiro Shirotani, Saijo (JP); Yohei Shimizu, Osaka (JP); Yasutomi Matsushima, Osaka (JP); Junichi Taniguchi, Osaka (JP)

(73) Assignee: KURARAY CO., LTD., Kurashiki (JP)

( * ) Notice: Subject to any disclaimer, the term of this patent is extended or adjusted under 35 U.S.C. 154(b) by 731 days.

(21) Appl. No.: 16/342,271

(22) PCT Filed: Nov. 1, 2017

(86) PCT No.: PCT/JP2017/039557
§ 371 (c)(1),
(2) Date: Apr. 16, 2019

(87) PCT Pub. No.: WO2018/088303
PCT Pub. Date: May 17, 2018

(65) Prior Publication Data
US 2019/0321235 A1    Oct. 24, 2019

(30) Foreign Application Priority Data
Nov. 9, 2016    (JP) .............................. JP2016-219235

(51) Int. Cl.
*A61F 13/02*    (2006.01)
*B32B 3/30*    (2006.01)
(Continued)

(52) U.S. Cl.
CPC ...... *A61F 13/0246* (2013.01); *A61F 13/0276* (2013.01); *B32B 27/12* (2013.01);
(Continued)

(58) Field of Classification Search
CPC ................ A61F 13/0203; A61F 13/025; A61F 13/0276; A61F 13/0289; A62F 13/0246; B32B 27/12; B32B 3/266; B32B 5/022
See application file for complete search history.

(56) References Cited

U.S. PATENT DOCUMENTS 3,073,304 A    1/1963    Schaar
2005/0271860 A1    12/2005    Quednau et al.
(Continued)

FOREIGN PATENT DOCUMENTS

CN    1114224 A    1/1996
CN    201459013 U    5/2010
(Continued)

OTHER PUBLICATIONS

Extended European Search Report dated May 18, 2020 in Patent Application No. 17868809.9, 7 pages.
(Continued)

*Primary Examiner* — Joanna Pleszczynska
(74) *Attorney, Agent, or Firm* — Element IP, PLC (57) ABSTRACT

A pressure-sensitive adhesive sheet including a pressure-sensitive adhesive layer is provided. The pressure-sensitive adhesive layer includes crater portions, each crater portion being concavely formed on an adhesive surface of the pressure-sensitive adhesive layer. A surface of the crater portion has a plurality of through holes.

15 Claims, 3 Drawing Sheets

(51) Int. Cl.
  *B32B 3/26* (2006.01)
  *B32B 5/02* (2006.01)
  *B32B 27/12* (2006.01)
  *C09J 201/00* (2006.01)
  *D04H 3/16* (2006.01)
  *B32B 27/40* (2006.01)

(52) U.S. Cl.
  CPC .............. *C09J 201/00* (2013.01); *D04H 3/16* (2013.01); *B32B 27/40* (2013.01)

(56) References Cited

U.S. PATENT DOCUMENTS

| | | | |
|---|---|---|---|
| 2007/0212520 | A1 | 9/2007 | Furumori et al. |
| 2009/0053467 | A1 | 2/2009 | Kato et al. |
| 2011/0160686 | A1 | 6/2011 | Ueda et al. |
| 2012/0116338 | A1* | 5/2012 | Ferry ..................... B32B 5/028 604/372 |
| 2015/0093557 | A1 | 4/2015 | Oka et al. |

FOREIGN PATENT DOCUMENTS

| | | |
|---|---|---|
| CN | 101969902 A | 2/2011 |
| JP | 50-4993 | 2/1975 |
| JP | 55-138452 | 10/1980 |
| JP | H-01-48019 B2 | 1/1986 |
| JP | S63-69879 A | 3/1988 |
| JP | 6-327756 A | 11/1994 |
| JP | 7-24049 A | 1/1995 |
| JP | 2000309764 A | 11/2000 |
| JP | 2003155459 A | 5/2003 |
| JP | 2004073232 A | 3/2004 |
| JP | 2004115774 A | 4/2004 |
| JP | 2005029907 A | 2/2005 |
| JP | 2007-99936 A | 4/2007 |
| JP | 2007314584 A | 12/2007 |
| JP | 2007330376 A | 12/2007 |
| JP | 2011121925 A | 6/2011 |
| KR | 1020050030650 A | 3/2005 |
| KR | 101086653 B1 | 11/2011 |
| WO | WO-2005028581 A1 | 3/2005 |
| WO | WO 2010/122665 A1 | 10/2010 |
| WO | WO-2012014589 A1 | 2/2012 |
| WO | WO-2013191187 A1 | 12/2013 |
| WO | WO 2014/132488 A1 | 9/2014 |

OTHER PUBLICATIONS

Decision for Grant of Patent dated Jul. 13, 2021 in Korean Patent Application No. 10-2019-7015585 (with English translation), 3 pages.

Information Offer Form issued Sep. 29, 2020 in Japanese Patent Application No. 2018-550166 (with English translation), 8 pages.

International Search Report dated Dec. 19, 2017 in PCT/JP2017/039557 filed Nov. 1, 2017.

Combined Chinese Office Action and Search Report dated Nov. 13, 2020 in Application No. 201780069350.5 (with English translation), 24 pages.

Office Action dated Jan. 21, 2021 in Korean Patent Application No. 10-2019-7015585 (with English translation), 10 pages.

Taiwanese Office Action dated Jul. 6, 2020 in Application No. 106138367 (with English translation), 13 pages.

Information Offer Form dated Nov. 2, 2021 in Japanese Patent Application No. 2018-550166 (with English translation).

Norimitsu Kaimai, "Melt-Blown Nonwoven Fabric", Tapyrus Co., Ltd., a Reference published in the website of All Nippon Nonwovens Association, publication date not available, reference received with Information Offer Form of Nov. 2, 2021 12 pages.

Office Action dated Dec. 7, 2021 in Japanese Patent Application No. 2018-550166 (with English translation).

* cited by examiner

PRESSURE-SENSITIVE ADHESIVE SHEET, ADHESIVE BANDAGE, AND METHOD OF PRODUCING THE SAME

TECHNICAL FIELD

The present invention relates to a pressure-sensitive adhesive sheet, an adhesive bandage, and methods of producing the pressure-sensitive adhesive sheet and the adhesive bandage.

BACKGROUND ART

Pressure-sensitive adhesive tapes for direct application to human skin, including those for medical use such as adhesive bandages and pressure-sensitive adhesive bandages and those for sports use such as athletic taping tapes, are required to have not only pressure-sensitive adhesive force but also a moisture-permeable property and a waterproof property. It is known that such pressure-sensitive adhesive tapes have a structure in which a pressure-sensitive adhesive agent layer is disposed on a support, for instance; and that a moisture-permeable property may be imparted to the support as well as the pressure-sensitive adhesive agent layer so that a good moisture-permeable property may be imparted to the resulting pressure-sensitive adhesive tape (see Japanese Patent Laying-Open No. 07-024049 (PTL 1) and Japanese Patent Laying-Open No. 2007-099936 (PTL 2), for example).

PTL 1 discloses a pressure-sensitive adhesive film for a first-aid adhesive bandage, in which the pressure-sensitive adhesive film is produced by applying a pressure-sensitive adhesive agent to a nonwoven fabric. According to PTL 1, a decrease in the moisture-permeable property may be prevented by imparting porosity to the pressure-sensitive adhesive agent that is to be applied to the nonwoven fabric and/or by carrying out pattern coating for the application of the pressure-sensitive adhesive agent. According to PTL 2, breathability may be improved by forming depressed portions, in a predetermined pattern, on a pressure-sensitive adhesive surface of a pressure-sensitive adhesive agent layer on a support layer.

CITATION LIST

Patent Literature

PTL 1: Japanese Patent Laying-Open No. 07-024049
PTL 2: Japanese Patent Laying-Open No. 2007-099936

SUMMARY OF INVENTION

Technical Problem

In order to impart porosity to the pressure-sensitive adhesive agent as described in PTL 1, a special material is required. In addition, either applying a pressure-sensitive adhesive agent by pattern coating as described in PTL 1 or forming depressed portions on a pressure-sensitive adhesive agent layer as described in PTL 2 is accompanied by the following problems, for instance: special-purpose equipment is required; and more steps are required for producing the pressure-sensitive adhesive sheet.

An object of the present invention is to provide a pressure-sensitive adhesive sheet and an adhesive bandage with a good moisture-permeable property both of which may be produced with no need for special equipment, and to provide methods of producing the pressure-sensitive adhesive sheet and the adhesive bandage.

Solution to Problem

The present invention is related to a pressure-sensitive adhesive sheet, an adhesive bandage, and methods of producing the pressure-sensitive adhesive sheet and the adhesive bandage, all of which are described below.

[1] A pressure-sensitive adhesive sheet including:
a substrate layer; and
a pressure-sensitive adhesive layer formed on the substrate layer,
the pressure-sensitive adhesive layer including crater portions, each crater portion being concavely formed on an adhesive surface of the pressure-sensitive adhesive layer,
the crater portion having a plurality of through holes on a surface of the crater portion.

[2] The crater portion includes first crater portions with an average diameter ranging from 0.04 to 0.8 mm, and
the number of the first crater portions per unit area of 1 $cm^2$ of the adhesive surface is 50 to 500.

[3] The total area of regions of the adhesive surface that are occupied by the crater portions is 5 to 50% of the total area of the adhesive surface.

[4] The through holes extend in a maze-like pattern.

[5] The substrate layer includes a nonwoven fabric, and
the pressure-sensitive adhesive layer is formed on the nonwoven fabric.

[6] The nonwoven fabric is a melt-blown nonwoven fabric.

[7] The nonwoven fabric has an average fiber diameter ranging from 0.5 to 20.0 µm.

[8] The pressure-sensitive adhesive sheet further includes a water-resistant layer, in which the water-resistant layer is disposed on a side of the substrate layer opposite another side of the substrate layer on which the pressure-sensitive adhesive layer is formed.

[9] An adhesive bandage including the pressure-sensitive adhesive sheet.

[10] A method of producing a pressure-sensitive adhesive sheet, the method including:
preparing a nonwoven fabric;
forming a pressure-sensitive adhesive layer on the nonwoven fabric; and
forming crater portions on an adhesive surface of the pressure-sensitive adhesive layer, the adhesive surface of the pressure-sensitive adhesive layer being a surface of the pressure-sensitive adhesive layer opposite a contact surface of the pressure-sensitive adhesive layer in contact with the nonwoven fabric, each crater portion being formed concavely toward the nonwoven fabric, and forming a plurality of through holes on a surface of the crater portion.

[11] The preparing a nonwoven fabric is carried out by forming the nonwoven fabric by melt blowing.

[12] A method of producing an adhesive bandage, the method including producing a pressure-sensitive adhesive sheet by the method described above.

Advantageous Effects of Invention

The present invention may provide a pressure-sensitive adhesive sheet and an adhesive bandage with a good moisture-permeable property both of which may be produced with no need for special equipment, and may also provide methods of producing the pressure-sensitive adhesive sheet and the adhesive bandage.

DESCRIPTION OF EMBODIMENTS

<Pressure-Sensitive Adhesive Sheet>

A pressure-sensitive adhesive sheet includes a pressure-sensitive adhesive layer and a substrate layer on which the pressure-sensitive adhesive layer is formed.

(Pressure-Sensitive Adhesive Layer)

Figure 1A:
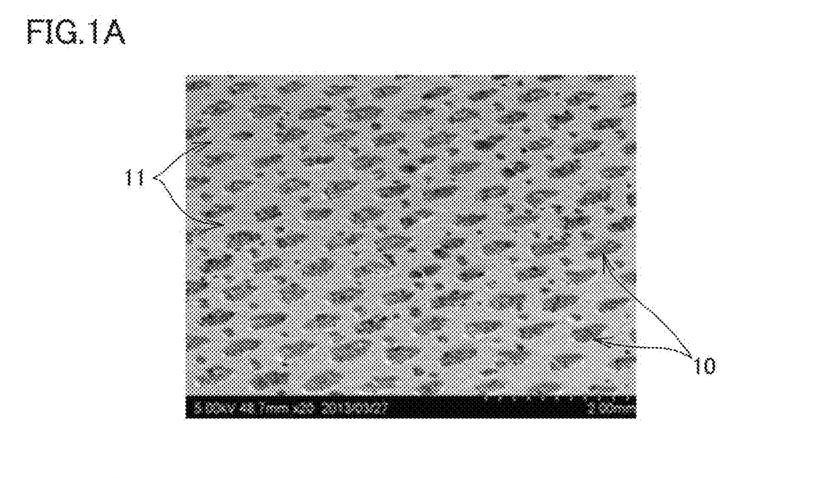
FIGS. 1A to 1C are SEM images of a pressure-sensitive adhesive layer of a pressure-sensitive adhesive sheet obtained in Example 1.
Figure 1B:
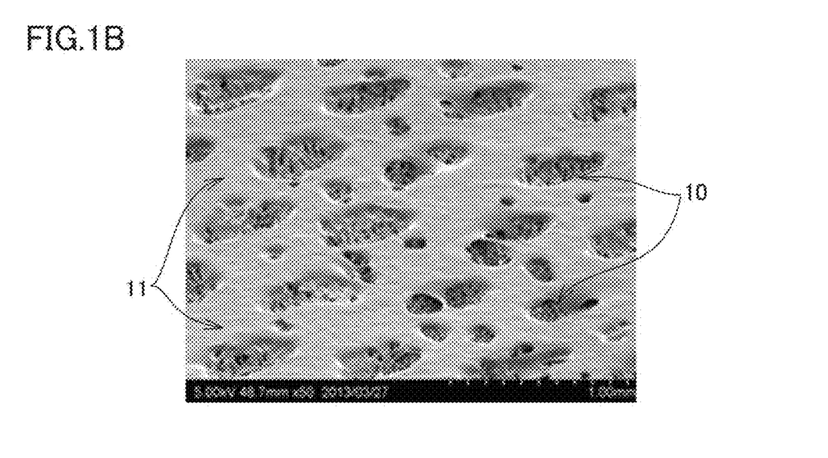
Figure 1C:
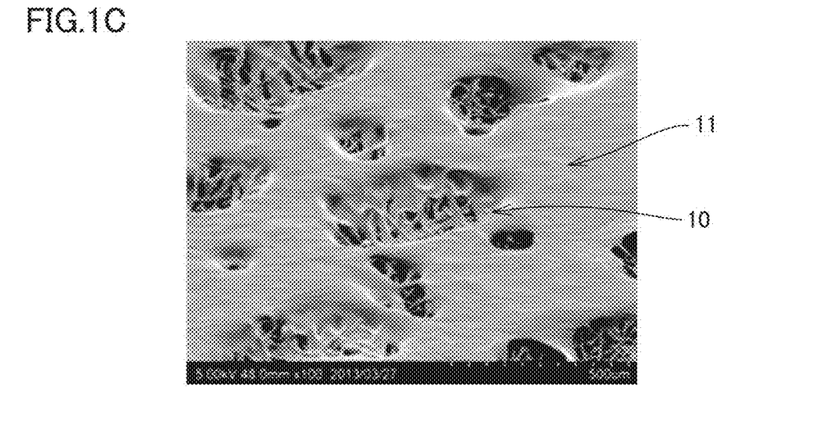

The pressure-sensitive adhesive layer includes a pressure-sensitive adhesive layer made of a pressure-sensitive adhesive agent. As shown in FIGS. 1A to 1C the pressure-sensitive adhesive layer includes an adhesive surface, which is to be put on a skin surface or the like; the pressure-sensitive adhesive layer includes a plurality of crater portions 10 on the adhesive surface thereof; the crater portions are formed concavely toward the opposite side of the pressure-sensitive adhesive layer; and the pressure-sensitive adhesive layer includes a flat portion 11, which is located between crater portions 10. The shape of each crater portion is not particularly limited and may be substantially circular, substantially elliptical, or substantially triangular, for example. The shape of each crater portion on the pressure-sensitive adhesive layer may be the same as or different from each other.

The average diameter of the crater portions is not particularly limited but is preferably 0.04 to 0.8 mm, more preferably 0.1 to 0.5 mm. The crater portion may include a crater portion with an average diameter outside the above range. The average diameter of the crater portions on the pressure-sensitive adhesive layer is calculated using an SEM image of the adhesive surface, and refers to the average diameter of regions each of which is a region on the pressure-sensitive adhesive layer defined by the interface between the flat portion and a crater portion. The average diameter is calculated using an SEM image of the crater portions. The specific calculation method involves the following steps: obtaining an image (about 2 mm×about 2 mm) of the adhesive surface of the pressure-sensitive adhesive sheet using an SEM; measuring a long diameter and a short diameter of a crater portion in the image using a scale bar, where the long diameter refers to the longest diameter of the crater portion and the short diameter refers to the shortest diameter of the crater portion; calculating the average of the long diameter and the short diameter thus measured; carrying out this average-diameter calculation for all the crater portions in the SEM image; and calculating the average of the resulting values and defining the resultant as the average diameter of the crater portions.

The crater portions include crater portions called first crater portions, which have an average diameter ranging from 0.04 to 0.8 mm. The number of the first crater portions per unit area of 1 cm$^2$ of the adhesive surface of the pressure-sensitive adhesive layer is preferably 50 to 500, more preferably 100 to 300. The average diameter may be calculated by the above-described calculation method. The number of the first crater portions per unit area of 1 cm$^2$ may be calculated by obtaining an image (about 2 mm×about 2 mm) using an SEM in the same manner as in the calculation of the average diameter, then counting crater portions in the image, and then using the resulting count to calculate the number of crater portions per unit area of 1 cm$^2$. With the number of crater portions per unit area being within the range described above, a good moisture-permeable property may be imparted to the pressure-sensitive adhesive layer. This configuration may further include a flat portion, which is located between the crater portions and has a predetermined area value. Therefore, in this configuration, nonuniformity in the pressure-sensitive adhesive force of the adhesive surface of the pressure-sensitive adhesive layer may be reduced and thereby a good pressure-sensitive adhesive force may be obtained.

Preferably, the crater portion has a plurality of through holes on its concave surface. For instance, the through holes form a three-dimensional network structure, within the pressure-sensitive adhesive layer, which is composed of a skeletal part consisting of a pressure-sensitive adhesive agent as well as hollow parts surrounded by the skeletal part. The shape of each through hole is not particularly limited. The number of the through holes per crater portion may be greater than one, preferably three or greater, more preferably ten or greater. The through holes may be linear holes communicating a front side (which is an adhesive surface side) of the crater portion with a back side (which is opposite the adhesive surface side) of the crater portion; curved holes communicating the front side with the back side in a maze-like pattern; or a combination of these two types.

These through holes of the crater portion may serve as pathways for a gas such as air to pass through the pressure-sensitive adhesive layer and, thereby, may impart a moisture-permeable property to the pressure-sensitive adhesive layer. The flat portion between the crater portions serves as a pressure-sensitive adhesive part, which is to be applied to a skin surface or the like and, as a result, may contribute to maintaining the pressure-sensitive adhesive force of the pressure-sensitive adhesive sheet. The total area of regions of the adhesive surface of the pressure-sensitive adhesive layer that are occupied by the crater portions is preferably 5 to 50%, more preferably 10 to 30%, of the total area of the adhesive surface (more specifically, of the total area of the crater portions combined with the total area of the flat portion). With the above-mentioned total area occupied by the crater portions being within the above range, the pressure-sensitive adhesive sheet may have a good balance between the moisture-permeable property and the pressure-sensitive adhesive force.

It is preferable that the crater portions and the flat portion be uniformly distributed so as to reduce nonuniformity in the pressure-sensitive adhesive force of the adhesive surface of the pressure-sensitive adhesive layer. More specifically, it is preferable that the crater portions be formed on the pressure-sensitive adhesive layer in such an arrangement that the distance (which is called pitch) between the centers of the crater portions is within a predetermined range. The pitch is preferably 500 to 1000 μm, more preferably 600 to 800 μm. Preferably, the crater portions are distributed in such a way that the crater portions with an average diameter ranging from 0.04 to 0.8 mm are aligned on a straight line. The expression "(the crater portions are) aligned on a straight line" refers to a distribution pattern in which at least some of the crater portions are located on a hypothetical straight line with a width ranging from 100 to 400 μm. The crater portions may be aligned on a single straight line or may be aligned on two or more straight lines.

The pressure-sensitive adhesive agent used for forming the pressure-sensitive adhesive layer may be any pressure-sensitive adhesive agent that is normally used in a pressure-sensitive adhesive sheet for such applications as medical care and sports and that adheres to the skin in a pressure-sensitive manner without causing much skin irritation. Specific examples of the pressure-sensitive adhesive agent include natural-rubber-based pressure-sensitive adhesive agents, synthetic-rubber-based pressure-sensitive adhesive agents, acrylate-based pressure-sensitive adhesive agents, styrene-isoprene-(SIS)-block-copolymer-based pressure-sensitive adhesive agents, silicone-based pressure-sensitive adhesive agents, and urethane-based pressure-sensitive adhesive agents. The thickness of the flat portion of the pressure-sensitive adhesive layer is preferably 10 to 100 μm, more preferably 30 to 60 μm. The weight per unit area of the flat portion of the pressure-sensitive adhesive layer is preferably 10 to 100 $g/m^2$, more preferably 30 to 60 $g/m^2$.

The viscosity of the pressure-sensitive adhesive agent during application is preferably 1000 cP to 4000 cP, more preferably 2000 cP to 3000 cP, from the viewpoint of forming concave craters having a plurality of through holes in the pressure-sensitive adhesive layer.

(Substrate Layer)

The pressure-sensitive adhesive sheet includes a substrate layer on which the pressure-sensitive adhesive layer is formed. The substrate layer may have a monolayer structure or a multilayer structure consisting of two or more layers. Preferably, at least a particular layer on which the pressure-sensitive adhesive layer is formed is a nonwoven fabric. In the configuration in which the substrate layer consists of two or more layers, the substrate layer may be formed by stacking nonwoven fabrics or may be formed by stacking a nonwoven fabric and, for example, another material (such as a film, a paper, a foam, a net, and/or a fabric including a woven fabric and a knitted fabric). Preferably, the substrate layer is elastic.

The type of the nonwoven fabric is not particularly limited, and examples of the type of the nonwoven fabric include melt-blown nonwoven fabric, spunbonded nonwoven fabric, airlaid nonwoven fabric, thermobonded nonwoven fabric, spunlace nonwoven fabric, needle-punched nonwoven fabric, and chemical bonded nonwoven fabric. Among these, a melt-blown nonwoven fabric is preferable because it may be made of fibers with small fiber diameters. A melt-blown nonwoven fabric has a small fiber diameter, a high density, and a good skin feel and is therefore suitable for use in a pressure-sensitive adhesive sheet of an adhesive bandage. In the configuration in which a melt-blown nonwoven fabric, among others, is used as the layer on which the pressure-sensitive adhesive layer is formed, there may be no need for use of special equipment when forming crater portions and through holes in the pressure-sensitive adhesive layer by a method of producing a pressure-sensitive adhesive sheet, which is described below.

In the configuration in which a nonwoven fabric is used as the layer on which the pressure-sensitive adhesive layer is formed, various properties of the nonwoven fabric and the pressure-sensitive adhesive layer may be adjusted, in a manner described below, so as to cause the pressure-sensitive adhesive layer to partially sink into depressed areas on the surface of the nonwoven fabric and/or into space between constituent fibers of the surface of the nonwoven fabric. By this adjustment, the crater portions and the through holes may be formed. The nonwoven fabric on which the crater portions and the through holes are to be formed preferably has projected areas and depressed areas on the surface of the nonwoven fabric and also has regular space between the constituent fibers of the surface of the nonwoven fabric.

The nonwoven fabric that constitutes the layer on which the pressure-sensitive adhesive layer is formed has an average fiber diameter ranging preferably from 0.5 to 20.0 μm, more preferably from 3.0 to 10.0 μm. With the average fiber diameter of the nonwoven fabric being within the above range, an appropriate amount of space is formed between the fibers and thereby, after the pressure-sensitive adhesive layer is formed thereon, a plurality of through holes may be formed on the surfaces of the crater portions. In the configuration in which the average fiber diameter of the nonwoven fabric is smaller than the above range, the fibers are densely distributed with smaller space therebetween and thereby the through holes described above are less likely to be formed. The weight per unit area of the nonwoven fabric is preferably 10 to 100 $g/m^2$, more preferably 20 to 60 $g/m^2$. The density of the nonwoven fabric is preferably 0.1 to 0.6 $g/cm^3$, more preferably 0.2 to 0.4 $g/cm^3$.

The material of the nonwoven fabric that is included in the substrate layer is not particularly limited, and examples of the material include polyurethane-based, polyolefin-based, polyester-based, polyamide-based, and styrene-based copolymers. From the viewpoint of imparting elasticity to the substrate layer, elastomeric materials are preferably used, among these, and elastomers based on polyurethane, elastomers based on a styrene-olefin block copolymer, and the like are more preferably used.

(Water-Resistant Layer)

The pressure-sensitive adhesive sheet may further include a water-resistant layer on a side of the substrate layer opposite another side of the substrate layer on which the pressure-sensitive adhesive layer is formed. With the water-resistant layer thus included, water resistance and strength may be imparted to the pressure-sensitive adhesive sheet. As the water-resistant layer, a moisture-permeable film is preferably used so as to maintain the moisture-permeable property of the pressure-sensitive adhesive sheet. The moisture permeability of the water-resistant layer is preferably not lower than 500 $g/m^2 \cdot 24$ h, more preferably not lower than 1000 $g/m^2 \cdot 24$ h. The thickness of the water-resistant layer is preferably 5 to 50 μm, more preferably 8 to 40 μm. The thinner the water-resistant layer is, the higher the moisture-permeable property is.

The water-resistant layer is preferably elastic so that the water-resistant layer does not interfere with the elasticity of the pressure-sensitive adhesive sheet. In order to impart elasticity to the water-resistant layer, it is preferable to use an elastomeric film and it is more preferable to use a thermoplastic elastomer such as polyurethane-based, polyolefin-based, polyester-based, polyamide-based, and styrene-based copolymers. The water-resistant layer may consist of a single layer or may consist of two or more layers. In the configuration in which the water-resistant layer consists of two or more layers, the layers may be made of the same material or may be made of different materials.

For the purpose of preventing water penetration into the substrate layer, water-repellent treatment may be applied, instead of or in addition to forming the water-resistant layer, to the side of the substrate layer opposite another side of the substrate layer on which the pressure-sensitive adhesive layer is formed. The water-repellent treatment may be carried out by applying a water repellent and/or a sizing agent to the surface of the substrate layer or by impregnating the surface of the substrate layer with a water repellent and/or a sizing agent. Examples of the water repellent include silicone-based water repellents, fluorine-based water repellents, and waxes. Examples of the sizing agent include rosin-based sizing agents and acrylic-based sizing agents.

(Release Sheet)

The pressure-sensitive adhesive sheet may further include a release sheet, which covers the pressure-sensitive adhesive layer. The release sheet may be a release sheet that is typically used in a pressure-sensitive adhesive sheet for skin application. For example, the release sheet may be a paper sheet or a film that is surface-coated with a release agent such as a silicone resin or a fluorine-based resin.

(Physical Properties of Pressure-Sensitive Adhesive Sheet)

The pressure-sensitive adhesive sheet that has a structure consisting of the water-resistant layer, the substrate layer, and the pressure-sensitive adhesive layer formed in this order preferably has a moisture permeability not lower than 800 $g/m^2 \cdot 24$ h, more preferably not lower than 1000 $g/m^2 \cdot 24$ h, further preferably not lower than 2000 $g/m^2 \cdot 24$ h. The moisture permeability may be measured by a measurement method described below in the Examples section.

The pressure-sensitive adhesive sheet on which the crater portions and the through holes are formed may have a structure in which the pressure-sensitive adhesive layer partially enters into the space between the fibers of the nonwoven fabric that is included in the substrate layer, as described below. The extent (more specifically, the amount and the depth) of the pressure-sensitive adhesive layer having entered into the space in the nonwoven fabric may be evaluated based on the pressure-sensitive adhesive force measured at the interface between the nonwoven fabric of the substrate layer and the pressure-sensitive adhesive layer. The pressure-sensitive adhesive force between the nonwoven fabric of the substrate layer and the pressure-sensitive adhesive layer may be evaluated by a measurement method according to JIS L1086.

<Method of Producing Pressure-Sensitive Adhesive Sheet>

A method of producing a pressure-sensitive adhesive sheet that includes crater portions and in which each crater portion has a plurality of through holes on the surface thereof includes, for example, the following steps:

preparing a nonwoven fabric;

forming a pressure-sensitive adhesive layer on the nonwoven fabric; and forming crater portions on an adhesive surface of the pressure-sensitive adhesive layer, the adhesive surface of the pressure-sensitive adhesive layer being a surface of the pressure-sensitive adhesive layer opposite a contact surface of the pressure-sensitive adhesive layer in contact with the nonwoven fabric, each crater portion being formed concavely toward the nonwoven fabric, and forming a plurality of through holes on a surface of the crater portion.

The crater portions and the through holes may be formed by, for instance, applying a pressure-sensitive adhesive agent to the projected and depressed surface of the nonwoven fabric and carrying out setting treatment.

The nonwoven fabric that is included in the substrate layer may be produced by melt blowing, spunbonding, airlaying, thermobonding, spunlacing, needle-punching, and/or chemical bonding. Among these, melt blowing is preferable for the production. A particularly preferable type of melt blowing is a process that involves extruding a hot-melt raw material resin through a die of a melt extruder while supplying a high-speed, high-temperature airstream and allowing the resulting fibers to be accumulated on a conveyor belt net. This type of melt blowing that involves accumulating fibers on a conveyor belt net is preferable because of its capability of forming moderately projected areas and moderately depressed areas on the surface of the nonwoven fabric on which the pressure-sensitive adhesive layer is formed. Preferably, the distance between projections and the distance between depressions on the conveyor belt net are 0.5 to 1.5 mm, for example. Preferably, the height of a projection of the conveyor belt net is 0.03 to 0.1 mm, for example. The height of a projection of the conveyor belt net is measured at the intersection of constituent fibers of the conveyor belt net where one or some of these fibers extend over the other, and refers to the distance between the bottom side of the bottom fiber to the top side of the top fiber. It should be noted that the constituent fibers of the conveyor belt net crossing each other at the intersections are in collapsed or curved shape, and therefore the above-mentioned height does not necessarily correspond to the calculation from the fiber diameter of the constituent fibers of the conveyor belt net. In the configuration in which the nonwoven fabric is produced by accumulating fibers on a conveyor belt net, it is preferable that the pressure-sensitive adhesive layer be formed on a conveyor-belt-net side of the nonwoven fabric that was in contact with the conveyor belt net. This is because the conveyor-belt-net side has projected areas attributable to the contour of the conveyor belt net, which tends to allow uniform formation of the crater portions upon formation of the pressure-sensitive adhesive layer.

Forming the pressure-sensitive adhesive layer on the nonwoven fabric may be carried out by applying a pressure-sensitive adhesive agent to the nonwoven fabric, or by applying a pressure-sensitive adhesive agent to a sheet of process paper and then transferring the resulting pressure-sensitive adhesive layer onto the nonwoven fabric.

The inventors of the present invention have found the following: when the nonwoven fabric on which the pressure-sensitive adhesive layer is formed has a particular surface profile, or when the pressure-sensitive adhesive layer has a particular set of physical properties, or when both these conditions are satisfied, the pressure-sensitive adhesive layer partially curves concavely toward the nonwoven fabric immediately after the pressure-sensitive adhesive layer is formed on the nonwoven fabric, or after the pressure-sensitive adhesive layer is left for a predetermined period of time for setting, and, as a result, concave crater portions are formed on the pressure-sensitive adhesive layer and a plurality of through holes are formed on the surfaces of the crater portions. The cause of this formation of the crater portions and the through holes is unclear, but a potential cause is as follows: after the pressure-sensitive adhesive layer is formed on the nonwoven fabric, the pressure-sensitive adhesive layer sinks into the depressed areas on the surface of the nonwoven fabric and into the space between the fibers; and, thereby, the pressure-sensitive adhesive layer partially curves concavely toward the nonwoven fabric to form concave crater portions. Furthermore, the thickness of the pressure-sensitive adhesive layer at the crater portions, which have sunk, is thinner than the thickness of the pressure-sensitive adhesive layer at the flat portion, which has not sunk. At these thinner areas, the pressure-sensitive adhesive layer further sinks into the space between the fibers of the nonwoven fabric and thereby a plurality of through holes are formed in the pressure-sensitive adhesive layer.

As the causes of the sinking of the pressure-sensitive adhesive layer, the following factors are considered as examples: the sizes of the projected areas and the depressed areas on the surface of the nonwoven fabric; the size of the space between the fibers on the surface of the nonwoven fabric; the extent of the affinity of the pressure-sensitive adhesive agent for the surface of the nonwoven fabric; and the deformability of the pressure-sensitive adhesive layer. It is considered that as a result of these factors affecting each other, the pressure-sensitive adhesive layer sinks in.

Formation of the crater portions and the through holes may be achieved by, for instance, adjusting the surface profile of the nonwoven fabric in a manner that is described below in the Examples section. For instance, projected areas and depressed areas may be formed on the surface of the nonwoven fabric by adjusting the profile of the projections and the depressions on the surface of an object, such as a conveyor belt net, that is used for collecting fibers for nonwoven fabric formation during nonwoven fabric production.

As another way for forming projected areas and depressed areas on the nonwoven fabric, the nonwoven fabric after production may be embossed so that projected areas and depressed areas are formed on the nonwoven fabric. Embossing involves hot-pressing the nonwoven fabric. Therefore, at the resulting projected areas and depressed areas, the fibers of the nonwoven fabric may have been compressed or converted into resin, for instance, and as a result, the space between the fibers may be reduced and thereby sinking of the pressure-sensitive adhesive layer may be limited. For this reason, it is preferable that embossing for forming projected areas and depressed areas involve adjusting the extent of melting and/or the extent of compression of the nonwoven fabric caused by hot-pressing so as to control the space between the fibers of the nonwoven fabric.

The deformability of the pressure-sensitive adhesive layer may be adjusted by changing, for example, the type and the weight average molecular weight of the pressure-sensitive adhesive agent used in the pressure-sensitive adhesive layer, the amount of a softening agent or the like added, the solvent content adopted for application and formation of the pressure-sensitive adhesive layer, and/or the hardening conditions and the drying temperature for the pressure-sensitive adhesive agent.

The crater portions and the through holes are formed as a result of the pressure-sensitive adhesive layer sinking into the nonwoven fabric side of the substrate layer while, for instance, the pressure-sensitive adhesive layer is rested for a particular period of time, or the pressure-sensitive adhesive layer is subjected to setting at a temperature from 30 to 60° C., after formation of the pressure-sensitive adhesive layer on the nonwoven fabric of the substrate layer. The duration of setting is not particularly limited and is preferably about three days to about two weeks.

(Formation of Water-Resistant Layer)

The method of producing a pressure-sensitive adhesive sheet may further include forming a water-resistant layer. For instance, the water-resistant layer may be formed by first forming the substrate layer and then applying a resin to the surface of the substrate layer, in which the resin is used for forming the water-resistant layer; or by first applying a resin to a surface of a sheet of process paper and then transferring the resulting resin-applied layer onto the surface of the substrate layer, in which the resin is used for forming the water-resistant layer. In the configuration in which water-repellent treatment is applied to the substrate layer, the water-repellent treatment may be carried out after the substrate layer is formed.

(Formation of Release Sheet)

The method of producing a pressure-sensitive adhesive sheet may further include forming a release sheet. The release sheet may be stacked on the pressure-sensitive adhesive layer that has been formed on the nonwoven fabric of the substrate layer. Alternatively, the process paper used in transferring the pressure-sensitive adhesive layer onto the nonwoven fabric of the substrate layer may be used as the release sheet.

<Adhesive Bandage>

By using the pressure-sensitive adhesive sheet, an adhesive bandage may be obtained. The adhesive bandage is formed by disposing a pad on a part of the pressure-sensitive adhesive layer of the pressure-sensitive adhesive sheet. The pad is used for covering the surface of a wound. The pad may be a nonwoven fabric, a gauze sheet, or a sponge, for example. The pad may be made of a liquid-absorptive material, including natural fibers such as cellulose fibers, regenerated cellulose fibers, and synthetic fibers.

<Method of Producing Adhesive Bandage>

The adhesive bandage may be produced by first producing the pressure-sensitive adhesive sheet and then stacking the pad on a part of the pressure-sensitive adhesive layer of the pressure-sensitive adhesive sheet.

EXAMPLES

[SEM Observation]

The surface of a pressure-sensitive adhesive layer was observed with an SEM (VE-8800, manufactured by Keyence Corporation).

[Average Diameter of Crater Portions]

The average diameter of crater portions was calculated using an SEM image of the crater portions. The specific calculation method involved the following steps: obtaining an image (about 2 mm×about 2 mm) using an SEM; measuring a long diameter and a short diameter of a crater portion in the image using a scale bar, where the long diameter referred to the longest diameter of the crater portion and the short diameter referred to the shortest diameter of the crater portion; calculating the average of the long diameter and the short diameter thus measured; carrying out this average-diameter calculation for all the crater portions in the SEM image; and calculating the average of the resulting values and defining the resultant as the average diameter of the crater portions.

[Calculation of Number of Crater Portions]

The number of crater portions was calculated using an SEM image of crater portions. The specific calculation method involved obtaining an image (about 2 mm×about 2 mm) using an SEM, then counting crater portions having an average diameter ranging from 0.04 to 0.8 mm in the image, and then using the resulting count to calculate the number of crater portions per unit area of 1 $cm^2$.

[Evaluation of Moisture-Permeable Property]

A pressure-sensitive adhesive sheet that was composed of a water-resistant layer, a nonwoven fabric layer, and a pressure-sensitive adhesive layer formed in this order was subjected to measurement by the cup method in accordance with JIS L 1099 using calcium chloride. A pressure-sensitive adhesive sheet with a moisture-permeable property not lower than 800 $g/m^2 \cdot 24$ h was rated as a pressure-sensitive adhesive sheet with a good moisture-permeable property.

[Evaluation of Pressure-Sensitive Adhesive Force]

Measurement was carried out in accordance with JIS L1086. A pressure-sensitive adhesive force not lower than 5 N/inch was rated as good.

Example 1

(Production of Nonwoven Fabric)

A thermoplastic polyurethane (trade name "T1190KS", manufactured by DIC Bayer Polymer Ltd.) was used as a polymer raw material. A melt extruder was prepared, which was equipped with orifices having a diameter of 0.3 mm arranged in line and with hot gas jet slits located on both sides of each orifice. Through each orifice of the melt extruder, the polymer raw material was discharged at a rate of 0.5 g/min at 240° C., which was the melting temperature of the polymer raw material. Through the jet slits of the melt extruder, hot air of the same temperature was jet out so as to cut the discharged polymer raw material into fine strips. The resulting fine strips were collected on a conveyor belt net, which was placed 30 cm below the melt extruder. Thus, a melt-blown polyurethane nonwoven fabric was obtained.

(Production of Water-Resistant Layer)

A mixed liquid for urethane film formation (a mixture of 100 parts by mass of "CRISVON KH-35" (manufactured by DIC Corporation), 10 parts by mass of dimethylformamide (DMF), 30 parts by mass of methyl ethyl ketone (MEK), and 4 parts by mass of a flesh color pigment) was applied with an applicator to a sheet of polypropylene process paper (which was used for urethane film formation) in such a way that the dry amount of the resulting coating was about 11 g/m². Thus, a resin-applied layer was formed. The resulting resin-applied layer was dried at 130° C. for one minute. Thus, a urethane film, which was to serve as a water-resistant layer, was formed on the process paper used for urethane film layer formation.

To the resulting urethane film formed on the process paper used for urethane film formation, an adhesive agent (composed of 100 parts by mass of "CRISVON 4070" (manufactured by DIC Corporation), 28 parts by mass of DMF, 15 parts by mass of "CRISVON DN-950" (manufactured by DIC Corporation), and 1 part by mass of "CRISVON T-81E" (manufactured by DIC Corporation)) was applied with a gravure roll coater (32 mesh) in such a way that the amount of the resulting coating before drying was about 15 g/m². Thus, an adhesive agent layer was formed. The resulting adhesive agent layer was dried at 130° C. for one minute. On this adhesive agent layer, the melt-blown nonwoven fabric obtained by the above process was stacked by thermocompression bonding at 80° C., followed by removing the process paper used for urethane film formation. Thus, a urethane-film-attached melt-blown nonwoven fabric was obtained.

(Production of Pressure-Sensitive Adhesive Layer)

A pressure-sensitive adhesive agent was prepared. The pressure-sensitive adhesive agent was composed of 100 parts by mass of "FINETACK CT-4040" (manufactured by DIC Corporation), 20 parts by mass of toluene (TOL), and 1 part by mass of "Coronate" (manufactured by Tosoh Corporation, with a viscosity of 200 cP), and had a viscosity of 2,500 cP. The pressure-sensitive adhesive agent was applied with an applicator to a sheet of process paper in such a way that the amount of the resulting coating before drying was about 35 g/m². Thus, a coating layer was formed. The resulting coating layer (a pressure-sensitive adhesive layer) was dried at 130° C. for one minute.

(Production of Pressure-Sensitive Adhesive Sheet)

To the coating layer (a pressure-sensitive adhesive layer) thus formed on the process paper, a nonwoven fabric side of the urethane-film-attached melt-blown nonwoven fabric was bonded, followed by setting at 40° C. for two weeks. Thus, a process-paper-attached pressure-sensitive adhesive sheet was obtained. From the resulting process-paper-attached pressure-sensitive adhesive sheet, the process paper was removed, and thus a pressure-sensitive adhesive sheet was obtained. The surface of the pressure-sensitive adhesive layer was observed with an SEM. The result is shown in FIGS. 1A to 1C. The average diameter of crater portions on the surface of the pressure-sensitive adhesive layer, the moisture-permeable property of the pressure-sensitive adhesive sheet, and the pressure-sensitive adhesive force of the pressure-sensitive adhesive sheet were evaluated. The results are shown in Table 1.

FIGS. 1A to 1C show the surface of the pressure-sensitive adhesive layer. As shown in FIGS. 1A to 1C, crater portions were formed on the pressure-sensitive adhesive layer and through holes were formed in the crater portions. In addition, crater portions of substantially the same shape and substantially the same size were aligned on straight lines. As shown in Table 1, the pressure-sensitive adhesive sheet had an excellent moisture-permeable property and a good pressure-sensitive adhesive force.

Example 2

A pressure-sensitive adhesive sheet was obtained in the same manner as in Example 1 except that setting was carried out at 60° C. for one week. The surface of a pressure-sensitive adhesive layer of the resulting pressure-sensitive adhesive sheet was observed with an SEM. The average diameter of crater portions on the surface of the pressure-sensitive adhesive layer, the moisture-permeable property of the pressure-sensitive adhesive sheet, and the pressure-sensitive adhesive force of the pressure-sensitive adhesive sheet were evaluated. Results are shown in Table 1.

According to the SEM observation of the surface of the resulting pressure-sensitive adhesive layer, crater portions and through holes were formed on the pressure-sensitive adhesive layer. The average diameter of the crater portions was smaller than that in Example 1. The pressure-sensitive adhesive sheet had a substantially good moisture-permeable property and a good pressure-sensitive adhesive force.

Example 3

Figure 2:
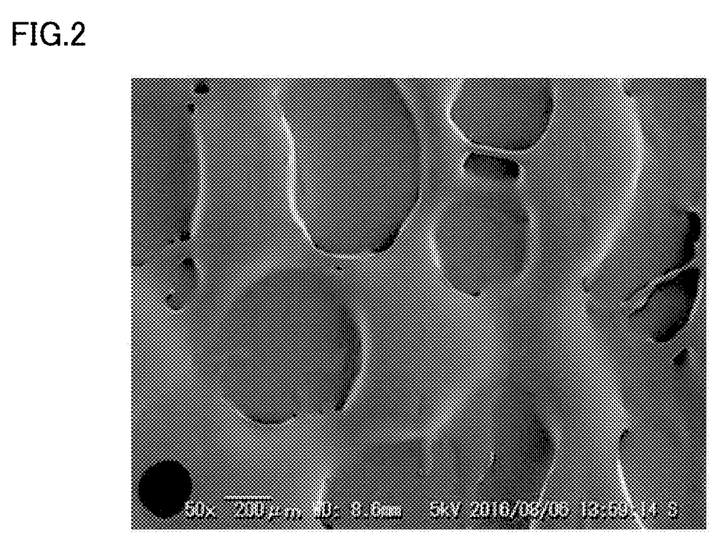
FIG. 2 is an SEM image of a pressure-sensitive adhesive layer of a pressure-sensitive adhesive sheet obtained in Example 3.

A melt-blown polyurethane nonwoven fabric was produced in the same manner as in Example 1. The resulting nonwoven fabric was used to obtain a pressure-sensitive adhesive sheet in the same manner as in Example 1 except that the nonwoven fabric was embossed and thereby the extent of projection of the projected areas and the extent of depression of the depressed areas were enhanced. The surface of the resulting pressure-sensitive adhesive layer was observed with an SEM, and the result is shown in FIG. 2. Table 1 lists the results of evaluation of the average diameter of crater portions on the surface of the pressure-sensitive adhesive layer, the moisture-permeable property of the pressure-sensitive adhesive sheet, and the pressure-sensitive adhesive force of the pressure-sensitive adhesive sheet.

According to the SEM observation of the surface of the pressure-sensitive adhesive layer, crater portions and through holes were formed on the pressure-sensitive adhesive layer. Although the pressure-sensitive adhesive force was low due to the large average diameter (1.0 mm) of the crater portions, a good moisture-permeable property was obtained.

Comparative Example

Figure 3:
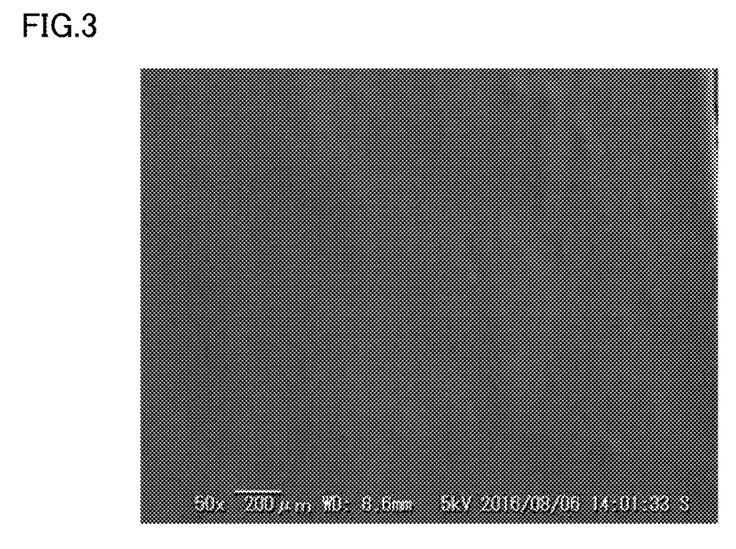
FIG. 3 is an SEM image of a pressure-sensitive adhesive layer of a pressure-sensitive adhesive sheet obtained in Comparative Example.

A melt-blown polyurethane nonwoven fabric was produced in the same manner as in Example 1. The resulting nonwoven fabric was used to prepare a pressure-sensitive adhesive sheet in the same manner as in Example 1 except that the nonwoven fabric was compressed with the use of smooth rolls and thereby the surface of the nonwoven fabric was made smooth. The surface of the pressure-sensitive adhesive layer was observed with an SEM, and the result is shown in FIG. 3. Table 1 lists the results of evaluation of the moisture-permeable property of the pressure-sensitive adhesive sheet and the pressure-sensitive adhesive force of the pressure-sensitive adhesive sheet.

As shown in FIG. 3, no crater portions or through holes were observed on the pressure-sensitive adhesive layer. Because of this, the pressure-sensitive adhesive sheet had a poor moisture-permeable property as shown in Table 1.

TABLE 1

|  | Example 1 | Example 2 | Example 3 | Comparative Example |
|---|---|---|---|---|
| Average diameter of crater portions [mm] | 0.36 | 0.17 | 1.0 | — |
| Number of crater portions [count/cm$^2$] | 190 | 205 | 49 | 0 |
| Moisture-permeable property [g/m$^2$/24 h] | 2397 | 1057 | 3110 | 558 |
| Pressure-sensitive adhesive force [N/inch] | 10.0 | 13.0 | 4.0 | 16.0 |

It should be construed that the embodiments and examples disclosed herein are given by way of illustration in all respects, not by way of limitation. It is intended that the scope of the present invention is defined by claims, not by the description above, and encompasses all modifications and variations equivalent in meaning and scope to the claims.

INDUSTRIAL APPLICABILITY

The pressure-sensitive adhesive sheet according to the present invention may be used as a tape for skin surface application, including adhesive bandages, pressure-sensitive adhesive bandages, body strengthening tapes used in chiropractic therapy and the like, body shaper tapes, and athletic taping tapes.

REFERENCE SIGNS LIST 10 crater portion; 11 flat portion

The invention claimed is:

1. A pressure-sensitive adhesive sheet, comprising:
a substrate layer, which is a monolayer structure of a nonwoven fabric;
a pressure-sensitive adhesive layer, which consists of a pressure-sensitive adhesive agent and is formed on and contacts a side of the substrate layer; and
a water-resistant layer, which is disposed directly, via an adhesive agent, on a side of the substrate layer opposite to the side of the substrate layer on which the pressure-sensitive adhesive layer is formed,
wherein:
the pressure-sensitive adhesive layer comprises crater portions, each crater portion being concavely formed on an adhesive surface of the pressure-sensitive adhesive layer,. which is a surface to be put on an object to which the pressure-sensitive adhesive sheet is applied;
the pressure-sensitive adhesive layer further comprises flat portions located between the crater portions on the adhesive surface;
the pressure-sensitive adhesive layer contacts the substrate layer directly at least at the flat portions; and
each crater portion has a plurality of through holes on a surface of the crater portion.

2. The pressure-sensitive adhesive sheet according to claim 1, wherein:
the crater portions include first crater portions with an average diameter ranging from 0.04 to 0.8 mm; and
a number of the first crater portions per unit area of 1 cm$^2$ of the adhesive surface is 50 to 500.

3. The pressure-sensitive adhesive sheet according to claim 1, wherein a total area of regions of the adhesive surface that are occupied by the crater portions is 5 to 50% of a total area of the adhesive surface.

4. The pressure-sensitive adhesive sheet according to claim 1, wherein the through holes comprise curved holes extending from one side of the crater portion to the other side of the crater portion in a maze-like pattern.

5. The pressure-sensitive adhesive sheet according to claim 1, wherein the nonwoven fabric is a melt-blown nonwoven fabric.

6. The pressure-sensitive adhesive sheet according to claim 1, wherein the nonwoven fabric has an average fiber diameter ranging from 0.5 to 20.0 μm.

7. The pressure-sensitive adhesive sheet according to claim 1, wherein the adhesive surface is opposite to a surface of the pressure-sensitive adhesive layer in contact with the nonwoven fabric.

8. The pressure-sensitive adhesive sheet according to claim 1, wherein the nonwoven fabric has projected areas and depressed areas so that the crater portions and the through holes are to be formed.

9. The pressure-sensitive adhesive sheet according to claim 8, wherein the projected areas and the depressed areas are formed by adjusting surface profile of the nonwoven fabric.

10. The pressure-sensitive adhesive sheet according to claim 8, wherein the projected areas and the depressed areas are formed by embossing.

11. The pressure-sensitive adhesive sheet according to claim 1, wherein the pressure-sensitive adhesive layer partially enters space between fibers of the nonwoven fabric.

12. An adhesive bandage, comprising the pressure-sensitive adhesive sheet according to claim 1.

13. A method of producing the pressure-sensitive adhesive sheet according to claim 1, the method comprising:
forming the substrate layer;
forming the pressure-sensitive adhesive layer on the nonwoven fabric;
forming the crater portions on the adhesive surface of the pressure-sensitive adhesive layer; and
forming the water-resistant layer, wherein:
the adhesive surface of the pressure-sensitive adhesive layer is a surface of the pressure-sensitive adhesive layer opposite to a surface of the pressure-sensitive adhesive layer in contact with the nonwoven fabric; and
each crater portion is formed concavely toward the nonwoven fabric.

14. The method of producing a pressure-sensitive adhesive sheet according to claim 13, wherein the nonwoven fabric is prepared by melt blowing.

15. A method of producing an adhesive bandage, the method comprising producing a pressure-sensitive adhesive sheet by the method according to claim 13.

* * * * *